United States Patent
Ichikawa et al.

(10) Patent No.: US 10,470,873 B2
(45) Date of Patent: Nov. 12, 2019

(54) INTRAOCULAR LENS AND HAPTIC FOR INTRAOCULAR LENS

(71) Applicant: CHUKYO MEDICAL CO., INC., Nagoya-shi, Aichi (JP)

(72) Inventors: Kazuo Ichikawa, Nagoya (JP); Norihiko Yoshida, Nagoya (JP)

(73) Assignee: CHUKYO MEDICAL CO., INC., Nagoya-shi, Aichi (JP)

( * ) Notice: Subject to any disclaimer, the term of this patent is extended or adjusted under 35 U.S.C. 154(b) by 0 days.

(21) Appl. No.: 16/090,384

(22) PCT Filed: Mar. 14, 2017

(86) PCT No.: PCT/JP2017/010098
§ 371 (c)(1),
(2) Date: Oct. 1, 2018

(87) PCT Pub. No.: WO2017/183359
PCT Pub. Date: Oct. 26, 2017

(65) Prior Publication Data
US 2019/0076238 A1    Mar. 14, 2019

(30) Foreign Application Priority Data
Apr. 18, 2016   (JP) .................................. 2016-082804

(51) Int. Cl.
*A61F 2/16*    (2006.01)
(52) U.S. Cl.
CPC .............. *A61F 2/1608* (2015.04); *A61F 2/16* (2013.01); *A61F 2/1613* (2013.01); *A61F 2/161* (2015.04);
(Continued)

(58) Field of Classification Search
CPC ............ A61F 2220/0016; A61F 2/1608; A61F 2002/16903; A61F 2002/1681;
(Continued)

(56) References Cited

U.S. PATENT DOCUMENTS 5,489,302 A * 2/1996 Skottun ................. A61F 2/1635
                                                                  623/6.13
6,197,057 B1   3/2001 Peyman et al.
(Continued)

FOREIGN PATENT DOCUMENTS

EP          3158974 A1    4/2017
JP       2003-512889 A    4/2003
(Continued)

OTHER PUBLICATIONS

Japanese Office Action Reasons for Refusal for Priority Japanese Application JP2016-082804, drafted on Jul. 11, 2016.

*Primary Examiner* — David H Willse
*Assistant Examiner* — Javier G Blanco
(74) *Attorney, Agent, or Firm* — Kenichiro Yoshida

(57) ABSTRACT

An intraocular lens 1 includes a lens 2 and a haptic 3 connected to the lens 2. The lens 2 is disposed behind an iris 7 in an eye of a patient. The haptic 3 has a main body 3a and first and second projections 3d and 3e. The main body 3a extends from the lens 2 outward in a radial direction about a visual axis C of the patient. The first and second projections 3d and 3e are located so as to project from the main body 3a toward spaces between a plurality of ciliary zonules 10 connecting a crystalline lens 11 and a ciliary body 8 in the eye. Accordingly, an intraocular lens and a haptic for an intraocular lens that are able to inhibit the position of a lens from being displaced are provided.

5 Claims, 7 Drawing Sheets

(52) U.S. Cl.
CPC ..... *A61F 2/1629* (2013.01); *A61F 2002/1682* (2015.04); *A61F 2002/1689* (2013.01); *A61F 2002/16903* (2015.04)

(58) Field of Classification Search
CPC ............ A61F 2002/1689; A61F 2/1629; A61F 2/161; A61F 2002/1682
See application file for complete search history.

(56) References Cited

U.S. PATENT DOCUMENTS

| | | | |
|---|---|---|---|
| 2002/0004682 A1* | 1/2002 | Zhou | A61F 2/1602 623/6.36 |
| 2008/0109078 A1* | 5/2008 | Rozakis | A61F 2/1613 623/6.43 |

FOREIGN PATENT DOCUMENTS

| | | |
|---|---|---|
| JP | 5436618 B2 | 12/2013 |
| JP | 2016-005521 A | 1/2016 |

\* cited by examiner

INTRAOCULAR LENS AND HAPTIC FOR INTRAOCULAR LENS

CROSS-REFERENCE TO RELATED APPLICATIONS

This present application is a National Stage entry of International Application No. PCT/JP2017/010098, filed Mar. 14, 2017, which claims priority to Japanese Patent Application No. 2016-082804, filed Apr. 18, 2016, which issued as Japanese Patent No. 6023378 on Oct. 14, 2016. The disclosures of the prior applications are incorporated by reference in their entirety.

FIELD OF THE INVENTION

The invention relates to an intraocular lens and a haptic for an intraocular lens.

BACKGROUND OF THE INVENTION

A treatment method in which an intraocular lens (an intraocular contact lens, a posterior chamber phakic intraocular lens) is implanted in an eye of a patient is known for improving the eyesight of the patient. Hitherto, regarding such an intraocular lens, the position of the lens mounted in an eye of a patient is fixed, and thus the lens focuses on an object located at a certain distance from the lens, but does not focus on an object located closer to or farther from the lens than the object.

Therefore, the present inventors have invented an intraocular lens that allows a patient having the intraocular lens mounted therein to adjust the focus by using relaxation/contraction movement of intraocular tissues (a ciliary body, a ciliary sulcus, etc.) (Patent Document 1).

CITATION LIST

Patent Document

Patent Document 1: Japanese Patent No. 5436618

SUMMARY OF INVENTION

Problems to be Solved by the Invention

Regarding the intraocular lens of Patent Document 1, the intraocular lens moves in response to relaxation/contraction movement of the intraocular tissues. Thus, the range where the intraocular lens is movable is required to fall within a specific region such that the position of the intraocular lens is not displaced from the region.

An object of the invention is to provide an intraocular lens and a haptic for an intraocular lens that are able to inhibit the position of a lens from being displaced.

Solution to the Problems and Effects of the Invention

An intraocular lens according the invention includes:
a lens disposed behind an iris in an eye of a patient
an elastically deformable plate-shaped leg portion extending from the lens outward in a radial direction about a visual axis of the patient along the radial direction; and
a projection portion projecting from the leg portion toward a space between a plurality of ciliary zonules connecting a crystalline lens and a ciliary body in the eye, wherein
the projection portion is interposed and held between the plurality of ciliary zonules, whereby force which is transmitted from the ciliary body through the plurality of ciliary zonules to the crystalline lens is transmitted through the projection portion to the leg portion.

The intraocular lens according to the invention includes the projection portion projecting from the leg portion, which extends from the lens, toward the space between the plurality of ciliary zonules connecting the crystalline lens and the ciliary body in the eye of the patient. In the eye of the patient, the ciliary body surrounding the crystalline lens of the patient in a ring shape is located, and the multiple thread-like ciliary zonules radially extend from the crystalline lens toward the ciliary body. Therefore, an annular space between the crystalline lens and the ciliary body are partitioned by the plurality of ciliary zonules, and, for example, a gap is formed therein by the adjacent ciliary zonules. In the intraocular lens according to the invention, since the projection portion projects in the gap, even when force that rotates the lens about the visual axis of the patient is accidentally applied to the lens, the projection portion becomes hooked to the ciliary zonule, and rotation of the lens is restricted. Therefore, it is possible to inhibit the position of the lens from being displaced.

In addition, a haptic for an intraocular lens according to the invention is a haptic for an intraocular lens, the haptic holding a lens, which is disposed behind an iris in an eye of a patient, in the eye of the patient, the haptic including:
an elastically deformable plate-shaped leg portion extending from the lens outward in a radial direction about a visual axis of the patient along the radial direction; and
a projection portion projecting from the leg portion toward a space between a plurality of ciliary zonules connecting a crystalline lens and a ciliary body in the eye, wherein
the projection portion is interposed and held between the plurality of ciliary zonules, whereby force which is transmitted from the ciliary body through the plurality of ciliary zonules to the crystalline lens is transmitted through the projection portion to the leg portion.

The invention is configured as a haptic for an intraocular lens (the above invention is configured as an intraocular lens) and can inhibit the position of the lens from being displaced, similar to the above invention of the intraocular lens.

In an embodiment of the invention, a first projection and a second projection are included as the projection portion, and are located about the visual axis.

According to this, the first and second projections make it possible to inhibit the position of the lens from being displaced.

In an embodiment of the invention, a first distance between the visual axis and the first projection and a second distance between the visual axis and the second projection as seen from a direction along the visual axis are different from each other.

According to this, the first and second projections having different distances to the visual axis make it possible to effectively inhibit the position of the lens from being displaced.

In an embodiment of the invention, a plurality of the first projections are formed around the visual axis.

According to this, the plurality of the first projections make it possible to inhibit the position of the lens from being displaced.

In an embodiment of the invention, a plurality of the second projections are formed around the visual axis.

According to this, the plurality of the second projections make it possible to inhibit the position of the lens from being displaced.

In an embodiment of the invention, a first distance between the visual axis and the first projection and a second distance between the visual axis and the second projection as seen from a direction along the visual axis are equal to each other.

According to this, the first and second projections having equal distances to the visual axis make it possible to inhibit the position of the lens from being displaced.

In an embodiment of the invention, each of the projection portions in the intraocular lens and the haptic for the intraocular lens is interposed and held between the plurality of ciliary zonules, whereby force which is transmitted from the ciliary body through the plurality of ciliary zonules to the crystalline lens is transmitted through the projection portion to the leg portion.

According to this, it is possible to make the leg portion move in conjunction with relaxation/contraction movement of the ciliary body. Thus, it becomes feasible to add action similar to that of a crystalline lens for adjusting the focus by relaxation/contraction of ciliary muscle in the eye, to the intraocular lens.

In an embodiment of the invention, the lens is a lens for correcting astigmatism of the patient.

According to this, it is possible to effectively inhibit the position of the lens for correction of astigmatism, which becomes useless when the lens mounted in the eye of the patient rotates about the visual axis of the patient (is displaced), from being displaced.

DESCRIPTION OF EMBODIMENTS

Figure 1A:
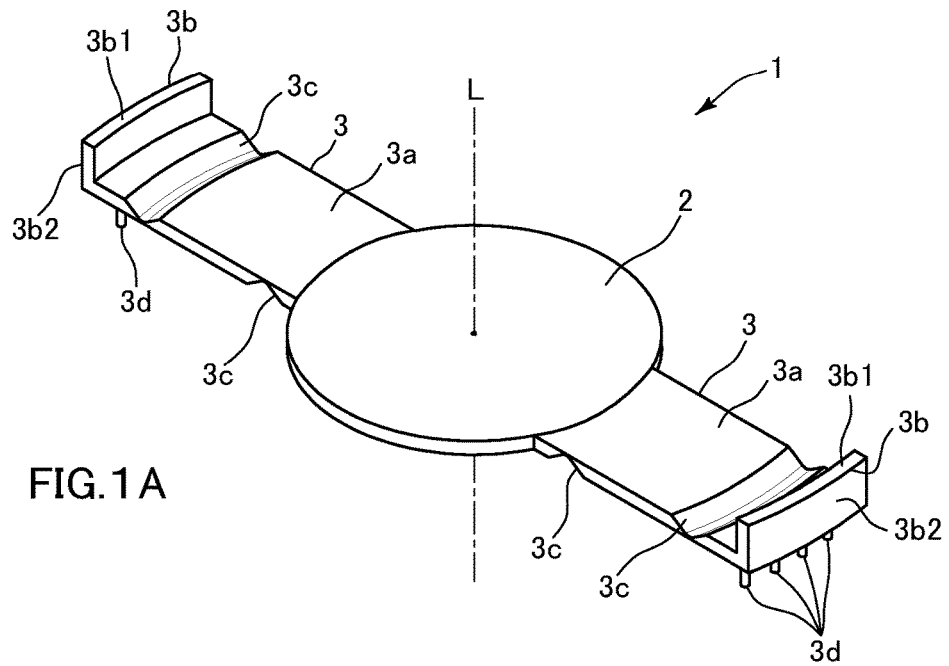
FIG. 1A is a schematic perspective view showing an example of the intraocular lens according to the invention.

FIGS. 1A to 1E show an intraocular lens 1 that is an example of the invention. The intraocular lens 1 is a so-called intraocular contact lens which is mounted in an eye of a patient with astigmatism (in front of a crystalline lens) in order to correct the astigmatism of the patient, and is elastically deformable at each portion.

The intraocular lens 1 includes a lens 2 and a haptic 3 extending from the lens 2. The lens 2 is formed in a disk shape so as to be elastically deformable and has a function to correct astigmatism of a patient with astigmatism. The lens 2 is disposed in the posterior chamber of the patient (a region behind the iris) and corrects the astigmatism of the patient. In FIGS. 1A to 1E, reference character L represents an axial line L passing through the center of a front surface of the lens 2. The axial line L coincides with the visual axis of the patient when the lens 2 is mounted in the eye of the patient. The present embodiment illustrates a lens for correcting astigmatism of a patient as the lens 2, but the lens 2 is not limited to a lens for correction of astigmatism, and may be a lens for correcting shortsightedness, farsightedness, or the like, or may be a lens serving as an artificial crystalline lens used for an operation for cataract.

The lens 2 is supported in the eye by the haptic 3. The haptic 3 is a portion for holding the lens 2 in the posterior chamber of the patient. In FIG. 1A, two haptics 3 are connected to the lens 2. Each haptic 3 is, for example, an elastically deformable material produced from an elastomer resin or the like, and may be formed as a member separate from the lens 2 and then joined to the lens 2 by a known method (for example, bonding with an adhesive). In addition, the same resin material may be used for the haptics 3 and the lens 2, and the haptics 3 may be produced so as to be integrated with the lens 2. Each haptic 3 has: a main body 3a extending from the outer edge of the lens 2 laterally relative to the lens 2; a projecting portion 3b projecting upward from the distal end of the main body 3a; recesses 3c located on a front surface and a back surface of the main body 3a; and first and second projections 3d and 3e (see FIG. 1B) projecting from the back surface of the main body 3a.

Figure 1B:
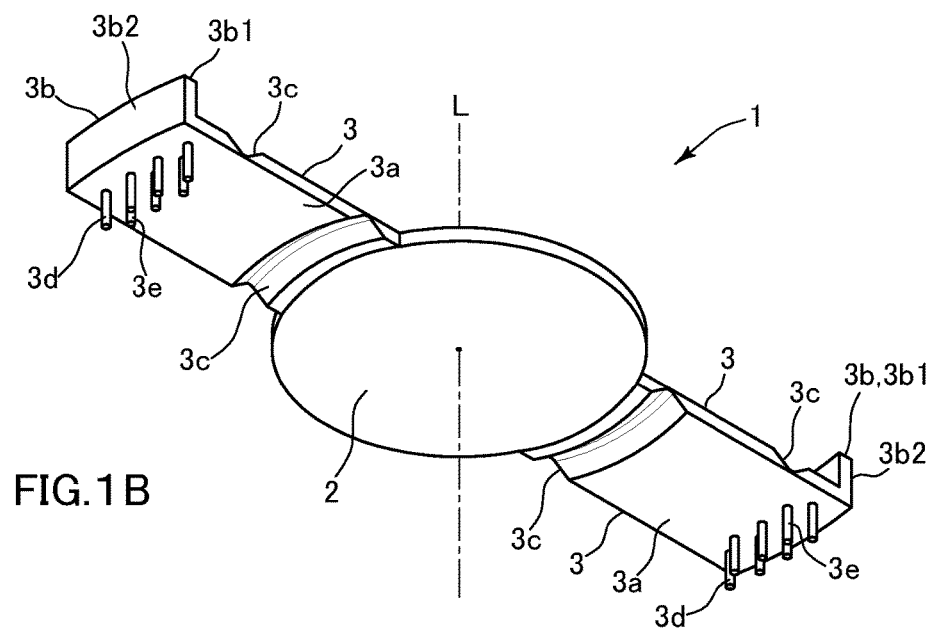
FIG. 1B is a schematic perspective view of the intraocular lens in FIG. 1A (a schematic perspective view as seen from a direction different from that of FIG. 1A).
Figure 1C:
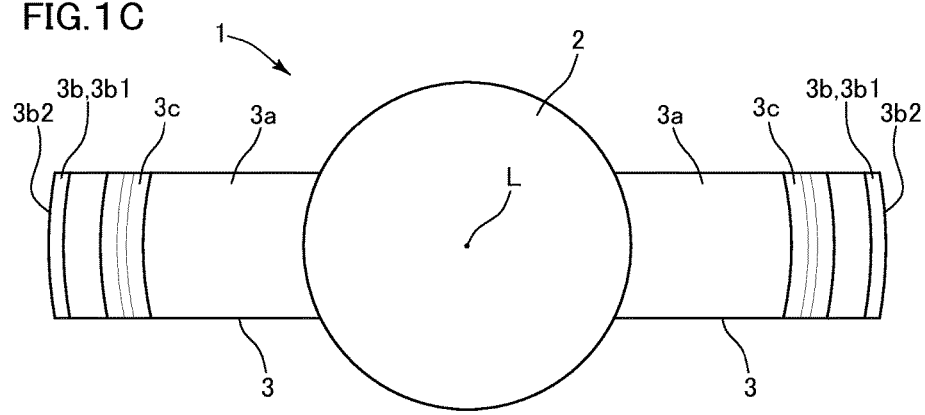
FIG. 1C is a schematic plan view of the intraocular lens in FIG. 1A.

The main body 3a is formed in a plate shape so as to be elastically deformable (see FIG. 1C). The main body 3a extends from the outer edge of the lens 2 straight outward in the radial direction about the axial line L (the radial direction when the axial line L in FIG. 1C is defined as a center). The main body 3a serves as a leg for holding the lens 2 in the eye of the patient.

The projecting portion 3b is formed so as to project from the distal end of the main body 3a upward along the axial line L as shown in FIG. 1A. The projecting portion 3b has: a projecting end portion 3b1 which is an end portion of the projecting portion 3b projecting along the axial line L; and a lateral end surface 3b2 which is an end surface located lateral to the axial line L. The lateral end surface 3b2 is a curved surface formed in an arc shape having a center at the axial line L in FIG. 1C. The projecting portion 3b is fixed in a state of being in contact with tissues in the eye and holds the lens 2 in the eye of the patient through the main body 3*a*. Thus, the projecting portion 3*b* also has a function as a medium to transmit movement of the intraocular tissues with which the projecting portion 3*b* is in contact, to the main body 3*a*.

Figure 1D:
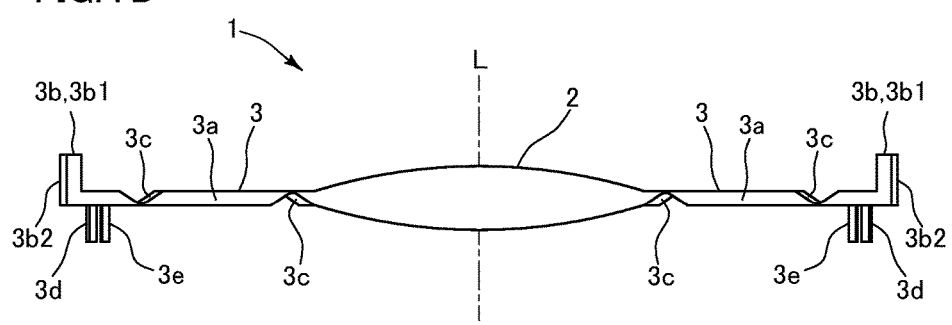
FIG. 1D is a schematic front view of the intraocular lens in FIG. 1A.
Figure 1E:
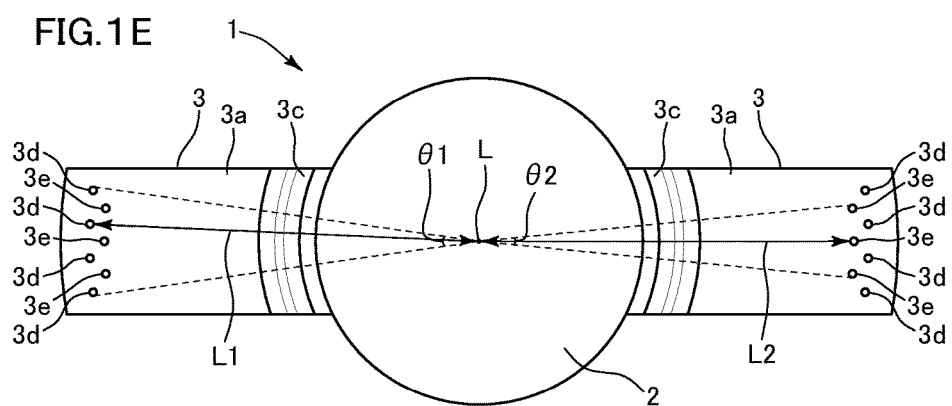
FIG. 1E is a schematic bottom view of the intraocular lens in FIG. 1A.

Each recess 3*c* is formed as a V-shaped groove that is formed on the front surface or the back surface of the main body 3*a* as shown in FIG. 1D so as to have an arc shape around the axial line L as shown in FIG. 1C or 1E. As shown in FIG. 1D, whereas the recess 3*c* at the front surface side of the main body 3*a* is located at the projecting portion 3*b* side, the recess 3*c* at the back surface side of the main body 3*a* is located at the lens 2 side. Each recess 3C is a portion that serves as a base point for elastically deforming the main body 3*a* in response to force applied to the main body 3*a*. For example, when force is applied from the projecting portion 3*b* or the first and second projections 3*d* and 3*e* to the main body 3*a*, the main body 3*a* elastically deforms based on the recesses 3*c*, so that the position of the lens 2 shifts along the axial line L.

A plurality of first projections 3*d* are disposed adjacently around the axial line L in a range of an acute angle θ1 about the axial line L as shown in FIG. 1E. Specifically, a plurality of first projections 3*d* are disposed at equiangular intervals (for example, 3- to 8-degree intervals) around the axial line L. In FIG. 1E, the distance between the first projection 3*d* and the axial line L is indicated by reference character L1. The distance L1 is the distance between the axial line L and the first projection 3*d* as seen from a direction along the axial line L. In addition, in FIG. 1E, similarly, a distance L2 (<L1) between the second projection 3*e* and the axial line L is indicated.

A plurality of second projections 3*e* are disposed adjacently around the axial line L in a range of an acute angle θ2 (<θ1) about the axial line L as shown in FIG. 1E. Specifically, a plurality of second projections 3*e* are disposed at the axial line L side with respect to the first projections 3*d* and at equiangular intervals (for example, 3- to 8-degree intervals) around the axial line L such that the first projections 3*d* and the second projections 3*e* alternate with each other around the axial line L. The present embodiment shows the example in which the intervals at which the first projections 3*d* are disposed around the axial line L are equal to the intervals at which the second projections 3*e* are disposed around the axial line L. However, the angular intervals at which the first projections 3*d* are disposed around the axial line L may be larger or smaller than the angular intervals at which the second projections 3*e* are disposed around the axial line L. In addition, the present embodiment shows the example in which the number of second projections 3*e* is smaller than the number of first projections 3*d*. However, the number of second projections 3*e* may be equal to or larger than the number of first projections 3*d*. The present embodiment shows the example in which the first projections 3*d* and the second projections 3*e* alternate with each other. However, it is possible for the first projections 3*d* and the second projections 3*e* to not alternate with each other.

Referring back to FIG. 1D, the first and second projections 3*d* and 3*e* are formed in a columnar shape and project downward from the back surface of the main body 3*a* between the projecting portion 3*b* and the recess 3*c* located at the front surface side of the main body 3*a*. The first and second projections 3*d* and 3*e* each have a diameter of 0.05 mm to 0.3 mm, for example, and each have a height of 0.2 mm to 2.1 mm, for example. The ratio of the diameter and the height of each of the first and second projections 3*d* and 3*e* is preferably in a range of diameter:height=1:4 to 1:7.

The intraocular lens 1 having the above configuration is mounted in an eye of a patient with astigmatism, for example. An example in which a doctor mounts the intraocular lens 1 in an eye of a patient will be described next. In the following, an example in which the doctor mounts the intraocular lens 1 in an eye of a patient without extracting a crystalline lens will be described.

Figure 2A:
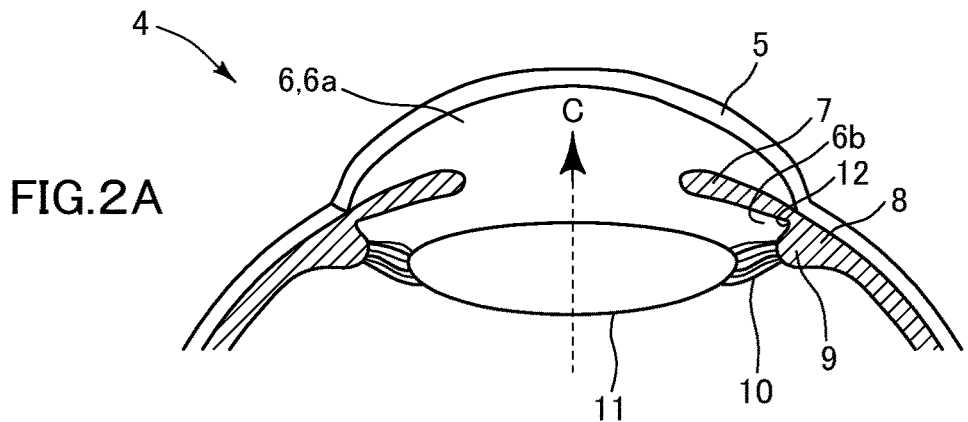
FIG. 2A is a schematic cross-sectional view schematically showing the interior of an eye of a patient.

FIG. 2A is a diagram schematically showing an eye 4 of a patient before the intraocular lens 1 is mounted. In FIG. 2A, an iris 7 located within an eye chamber 6 (between an anterior chamber 6*a* and a posterior chamber 6*b*) behind a cornea 5 is opened by a drug. A ciliary body 8 (ciliary muscle) is located in a circumferential direction about a visual axis C of the patient (the ciliary body 8 is annularly located), and ciliary processes 9 project from the ciliary body 8 toward the visual axis C and are connected to a crystalline lens 11 by ciliary zonules 10. In addition, a ciliary sulcus 12 is located between the ciliary processes 9 and the iris 7.

Figure 2B:
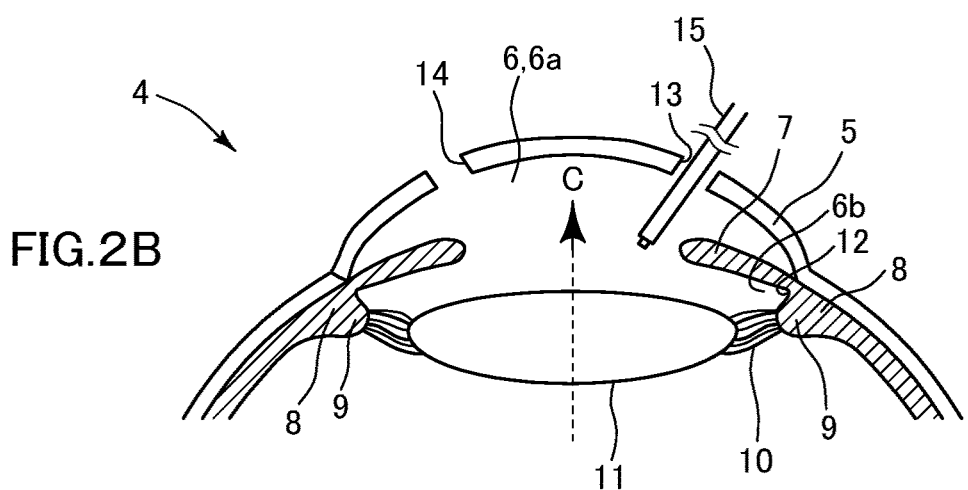
FIG. 2B is a schematic cross-sectional view showing a state where a tool is inserted into the eye in FIG. 2A.

The doctor partially incises the cornea 5 to form insertion holes 13 and 14 (FIG. 2A→FIG. 2B). For example, the insertion hole 13 is a hole for inserting an end of a tool (an injector 15), for inserting the intraocular lens 1 into the eye, into the eye, and the insertion hole 14 is a hole for inserting a pair of forceps (not shown), for operating the intraocular lens 1 inserted in the eye, into the eye.

The elastically deformable intraocular lens 1 is stored in the injector 15, which is inserted into the eye, for example, in a state where the intraocular lens 1 is in a tubular shape. The doctor inserts the end of the injector 15 having the intraocular lens 1 stored therein, through the insertion hole 13, and discharges the intraocular lens 1 through the end of the injector 15 into the posterior chamber 6*b*.

Figure 3A:
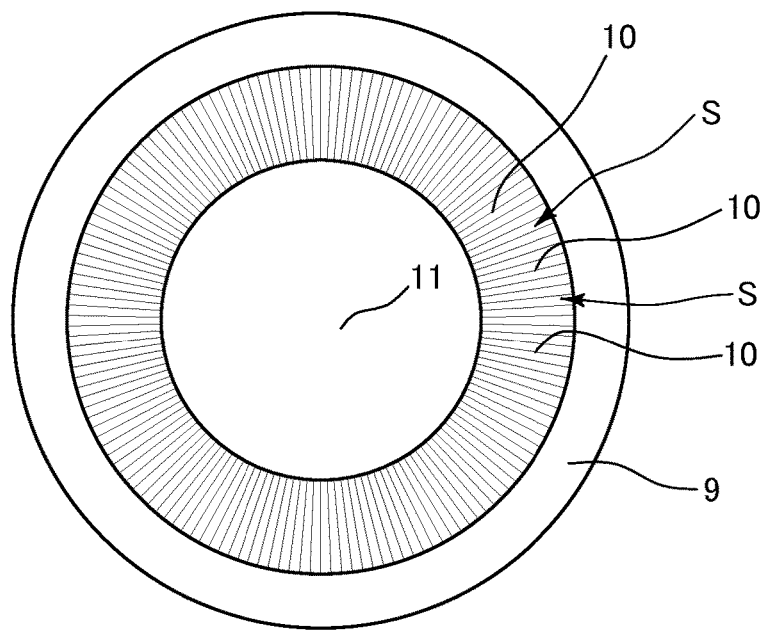
FIG. 3A is a schematic diagram schematically showing a crystalline lens, ciliary processes, and ciliary zonules in the eye as seen from the iris side.

Separately, the doctor inserts the pair of forceps (not shown) through the insertion hole 14 into the eye, and pinches one of the main bodies 3*a* (see FIG. 1A) of the intraocular lens 1 discharged into the eye. As shown in FIG. 2B, in the eye of the patient, the ciliary processes 9 are located in a ring shape so as to surround the crystalline lens 11, and the thread-like ciliary zonules 10 extend from respective portions of the ciliary processes 9 to the crystalline lens 11. When the crystalline lens 11 is seen from the posterior chamber 6*b* side, innumerable thread-like ciliary zonules 10 radially extend from the periphery of the crystalline lens 11 to the ciliary processes 9 as shown in FIG. 3A. Thus, the ciliary zonules 10 are stretched in an annular space between the crystalline lens 11 and the ciliary processes 9, and gaps S are formed in a mesh pattern around the crystalline lens 11 by the crystalline lens 11, the ciliary processes 9, and the ciliary zonules 10. Then, the doctor inserts the respective first and second projections 3*d* and 3*e* of the haptic 3 into the different gaps S such that the first and second projections 3*d* and 3*e* are each interposed between a pair of the ciliary zonules 10 (see FIG. 3B). Then, the doctor leads the projecting portion 3*b* of the main body 3*a* to the ciliary sulcus 12 shown in FIG. 2B with a state where the first and second projections 3*d* and 3*e* are inserted between the ciliary zonules 10 being maintained. Accordingly, the projecting portion 3*b* is inserted into the ciliary sulcus 12 such that the projecting end portion 3*b*1 and the lateral end surface 3*b*2 of the projecting portion 3*b* shown in FIG. 1A press and spread the ciliary sulcus 12, and the lateral end surface 3*b*2 is located so as to be in contact with the ciliary sulcus 12 or a portion adjacent to the ciliary sulcus 12. The lateral end surface 3*b*2 is brought into surface contact with the ciliary sulcus 12 or the portion adjacent to the ciliary sulcus 12 as described above, whereby the haptic 3 is assuredly fixed in the eye.

Figure 2C:
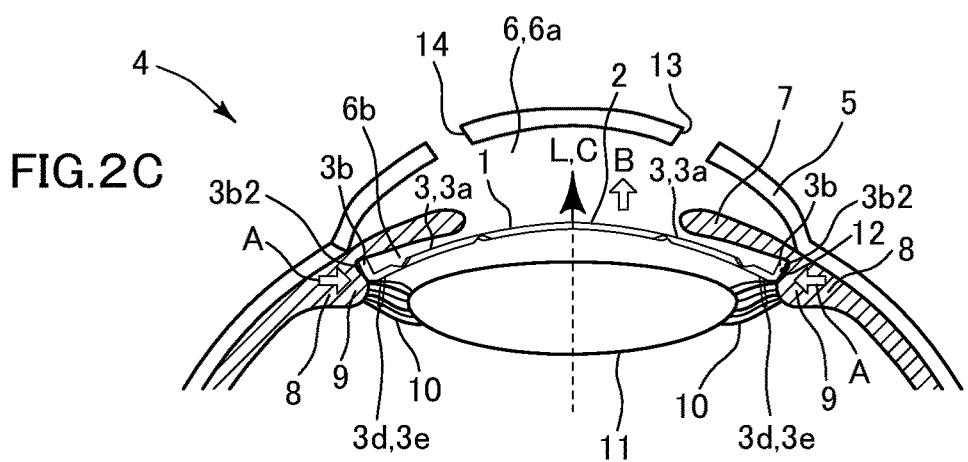
FIG. 2C is a schematic cross-sectional view showing a state where the intraocular lens in FIG. 1A is mounted in the eye of the patient subsequently to FIG. 2B.

The doctor performs the same operation on the other main body 3a, whereby the intraocular lens 1 can be assuredly held in the eye without suture (FIG. 2C). In this state, the lens 2 is located in the posterior chamber 6b such that the axial line L of the lens 2 coincides with the visual axis C of the eye of the patient. Thereafter, the doctor takes the pair of forceps, etc., out of the eyeball, and mounting the intraocular lens 1 to the patient with astigmatism is completed.

Figure 3B:
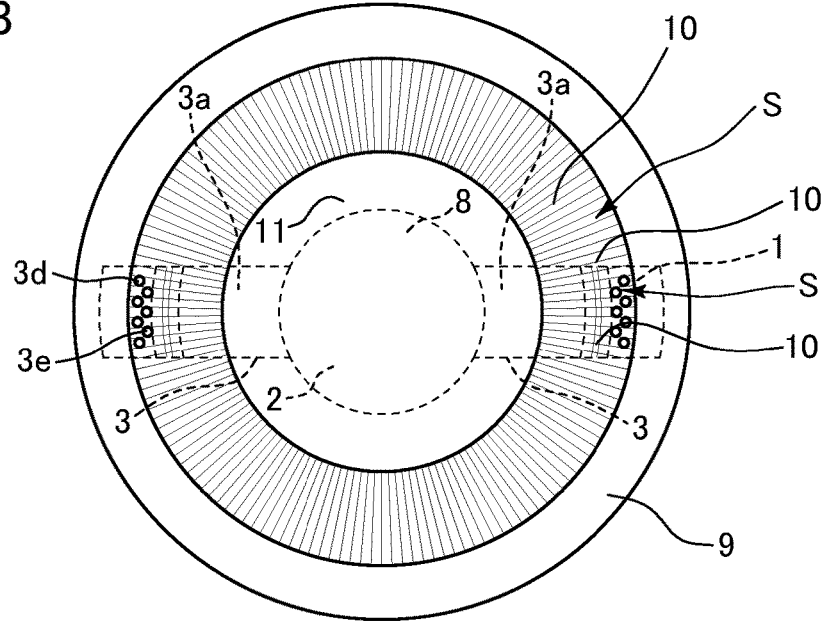
FIG. 3B is an explanatory diagram schematically showing a state where first and second projections of the intraocular lens in FIG. 1A are inserted into gaps demarcated by the crystalline lens, the ciliary processes, and the ciliary zonules in FIG. 3A.

In a state where the intraocular lens 1 is mounted in the eye of the patient, the lens 2 is held in the posterior chamber 6b behind the iris 7 in the eye of the patient. The main body 3a extends from the lens 2 toward intraocular tissues such as the ciliary sulcus 12 located around the visual axis C of the patient, and the first and second projections 3d and 3e project from the main body 3a toward the spaces between a plurality of the ciliary zonules 10 connecting the crystalline lens 11 and the ciliary processes 9. As shown in FIG. 3B, the first and second projections 3d and 3e are inserted into the gaps S so as to be interposed between the ciliary zonules 10 and are not in contact with the ciliary processes 9. Since the first and second projections 3d and 3e are disposed at the ciliary processes 9 side as shown in FIG. 3B, the first and second projections 3d and 3e and the crystalline lens 11 can be prevented from coming into contact with each other to damage the crystalline lens 11.

When the patient having the intraocular lens 1 mounted therein attempts to focus on a visual target (a target that the patient attempts to see), the ciliary body 8 relaxes or contracts in accordance with the position of the visual target. Therefore, each projecting portion 3b moves in conjunction with the ciliary body 8 through the lateral end surface 3b2 that is in surface contact with the ciliary sulcus 12 in FIG. 2C or the portion adjacent to the ciliary sulcus 12. For example, when the ciliary body 8 contracts (expands) to generate force shown by arrows A in FIG. 2C, the projecting portion 3b is pressed to the visual axis C side, and the elastically deformable haptics 3 deform so as to bulge in the frontward direction of the eye 4. Accordingly, the lens 2 moves in the direction of an arrow B in FIG. 2C (in the frontward direction of the eye 4). Then, when the force (arrows A) that expands the ciliary body 8 is eliminated, the elastic forces of the haptics 3 are released, and the lens 2 returns to the original position.

The first and second projections 3d and 3e of each haptic 3 are interposed and held between a plurality of the ciliary zonules 10 as shown in FIG. 3B. Thus, the ciliary zonules 10 tense or relax in response to relaxation or contraction of the ciliary body 8. Therefore, force generated from the ciliary processes 9 can be transmitted to the main body 3a also through the first and second projections 3d and 3e that are interposed and held between the ciliary zonules 10, and force of the tissues in the eye can be more effectively transmitted to the haptic 3.

Because of the above, the intraocular lens 1 allows the lens 2 to move back and forth in response to expansion and contraction of the ciliary body 8 as shown in FIG. 2C. Thus, it is possible for the patient to adjust the focus by using relaxation/contraction movement of the intraocular tissues (the ciliary body 8, the ciliary sulcus 12, etc.) of the patient.

The gaps S are formed in a mesh pattern by the multiple thread-like ciliary zonules 10 radially extending from the periphery of the crystalline lens 11 as shown in FIG. 3B, and the first and second projections 3d and 3e of the intraocular lens 1 are located so as to project in the gaps S. Thus, even when force that rotates the lens 2 about the visual axis C is accidentally generated and applied to the lens 2 mounted in the eye of the patient as shown in FIG. 2C, the first and second projections 3d and 3e become hooked to the ciliary zonules 10, whereby rotation of the lens 2 is restricted. Therefore, it is possible to inhibit the lens 2 from rotating about the visual axis C to displace the position of the lens 2.

The pluralities of first and second projections 3d and 3e are formed around the axial line L as shown in FIG. 1E. Thus, the pluralities of projections 3d and 3e make it possible to inhibit the position of the lens 2 from being displaced. In addition, since the distance L1 between the axial line L and the first projection 3d and the distance L2 between the axial line L and the second projection 3e are different from each other, the first and second projections 3d and 3e can effectively inhibit the position of the lens 2 from being displaced when force that rotates the lens 2 about the visual axis C (axial line L) is generated. Since the plurality of first projections 3d are disposed around the axial line L in the range of the acute angle θ about the axial line L, the first projections 3d are effective for inhibiting the position of the lens 2 from being displaced. The same applies to the second projections 3e.

When the first and second projections 3d and 3e are formed in a columnar shape as shown in FIG. 1B and the diameters thereof are in the range of 0.05 mm to 0.3 mm, the first and second projections 3d and 3e are easily inserted between the ciliary zonules 10. In addition, when the heights of the first and second projections 3d and 3e are in the range of 0.2 mm to 2.1 mm, the first and second projections 3d and 3e are less likely to come out from the gaps S, which are formed in a mesh pattern between the ciliary zonules 10. When the ratio of the diameter and the height is in the range of diameter:height=1:4 to 1:7, the first and second projections 3d and 3e are more effective.

Figure 4:
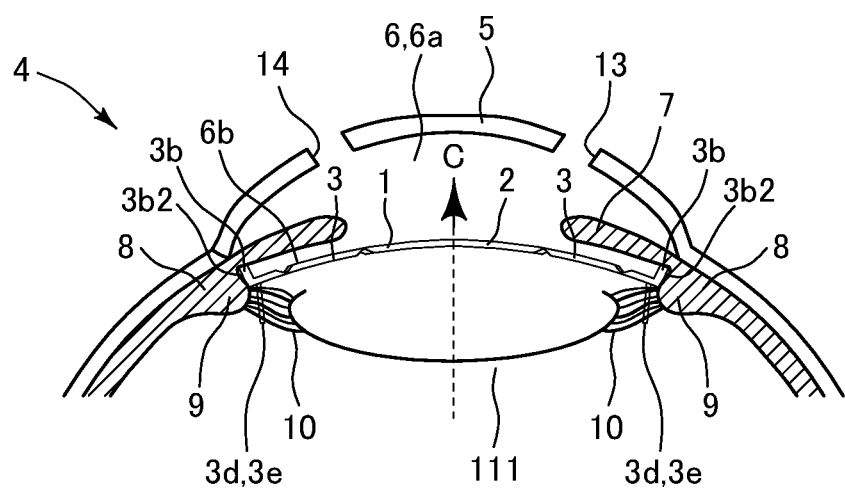
FIG. 4 is a schematic cross-sectional view showing a state where the intraocular lens in FIG. 1A is mounted on a crystalline lens in which a part of an anterior capsule and a posterior capsule remain.

In the above, the example in which the intraocular lens 1 is held in front of the crystalline lens 11 has been described. However, the intraocular lens 1 may be held in front of a crystalline lens 111 that is partially extracted as in FIG. 4. For example, after a large part of the crystalline lens is extracted with a part of the anterior capsule and the posterior capsule being left such that the connection between the ciliary zonules 10 and the crystalline lens 111 can be maintained, the intraocular lens 1 may be mounted in front of the crystalline lens 111 in the same manner as described above.

Figure 5:
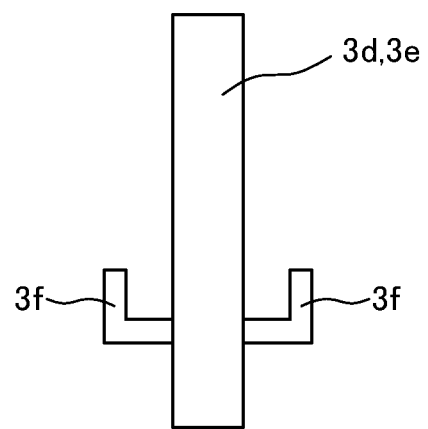
FIG. 5 is a schematic diagram showing Modification 1 of the first and second projections in FIG. 1A.

In the above, the intraocular lens 1 has been described as an example. However, the intraocular lens 1 is merely an embodiment, and various modifications are possible. For example, the shapes of the first and second projections 3d and 3e of the intraocular lens 1 are not limited to columnar shapes, and various shapes such as a conical shape, a circular truncated cone shape, and a rectangular parallelepiped shape can be adopted. In addition, hook portions 3f may be provided so as to project laterally from the side surfaces of the first and second projections 3d and 3e as shown in FIG. 5 such that the ciliary zonules 10 can be hooked thereto. Accordingly, the first and second projections 3d and 3e inserted between the ciliary zonules 10 formed in a mesh pattern as shown in FIG. 3A are less likely to come out. A plurality of hook portions 3f may be provided to each of the first or second projections 3d or 3e or to each of the first and second projections 3d and 3e.

Figure 6:
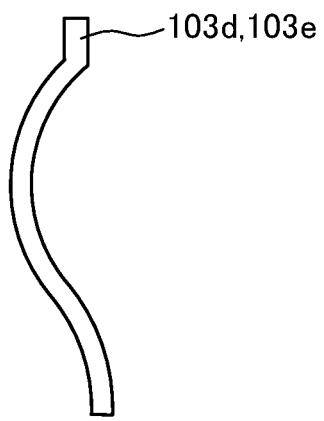
FIG. 6 is a schematic diagram showing Modification 2 of the first and second projections in FIG. 1A.

The shapes of the first and second projections 3d and 3e are not limited to geometric shapes, and may be, for example, shapes corresponding to the outer surfaces of the ciliary processes 9. For example, hook-shaped first and second projections 103*d* and 103*e* extending from base portions of the ciliary processes 9 along the outer surfaces of the ciliary processes 9 via anterior end portions of the ciliary processes 9 to base portions at the opposite side may be adopted (see FIG. 6). In this case, the first and second projections 103*d* and 103*e* may be mounted in the eye of the patient so as to extend along the outer surfaces of the ciliary processes 9. When the first and second projections 103*d* and 103*e* are mounted so as to extend along the ciliary processes 9, movement of the ciliary processes 9 can be transmitted directly to the haptic 3 through the first and second projections 103*d* and 103*e*. In this case, the second projections 103*e* may not be provided.

In the above description of FIGS. 2A to 2C, the example in which the first and second projections 3*d* and 3*e* are not in contact with the intraocular tissues other than the ciliary zonules 10 in a state where the intraocular lens 1 is mounted in the eye has been described. However, the intraocular lens 1 may be mounted in a state where the first projections 3*d* (the second projections 3*e* in some cases) are in contact with the ciliary processes 9, etc. In this case, for example, when the first projections 3*d* come into contact with the intraocular tissues, movement of the contacted intraocular tissues can be transmitted directly to the haptic 3 through the first projections 3*d*.

In the above, the example in which the two haptics 3 are connected to the lens 2 has been described. However, three, four, five, or more haptics 3 may be connected to the lens 2. In this case, the first and second projections 3*d* and 3*e* of each haptic 3 can inhibit the position of the lens 2 from being displaced. In addition, the shape extending in a plate shape from the axial line L toward the lateral side (the inner side of the eye interior of the patient) as shown in FIG. 1B has been exemplified for the main body 3*a* of each haptic 3. However, for the main body 3*a*, various shapes such as a shape extending linearly or in a curved manner can be adopted. In addition, in the above, the example in which the projecting portion 3*b* is in surface contact with the ciliary sulcus 12 has been described. However, the projecting portion 3*b* may be in contact with the intraocular tissues in a manner other than surface contact.

In the above, the intraocular lens 1 in which the haptics 3 move in conjunction with the intraocular tissues has been described as an example. However, projection portions such as the first and second projections 3*d* and 3*e* can be applied to an intraocular lens that does not move in conjunction with the intraocular tissues. Accordingly, it is possible to inhibit the position of the lens from being displaced from a normal position in the eye, and, for example, the invention may be applied to an intraocular lens that requires suture in order to hold the intraocular lens in an eye.

Although the embodiments of the invention have been described above, the invention is not limited to the specific description thereof, and the illustrated configurations, processes, and the like can be combined as appropriate within a range where there is no technical contradiction, to practice the invention, or a certain element or process can be substituted with a known form to practice the invention.

Figure 7:
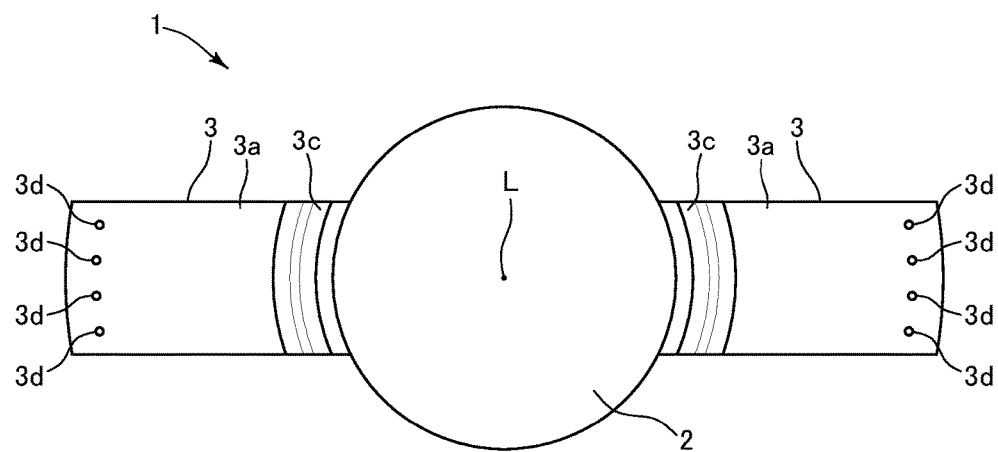
FIG. 7 is a schematic bottom view showing an intraocular lens obtained by removing the second projections from the intraocular lens in FIG. 1E.
Figure 8:
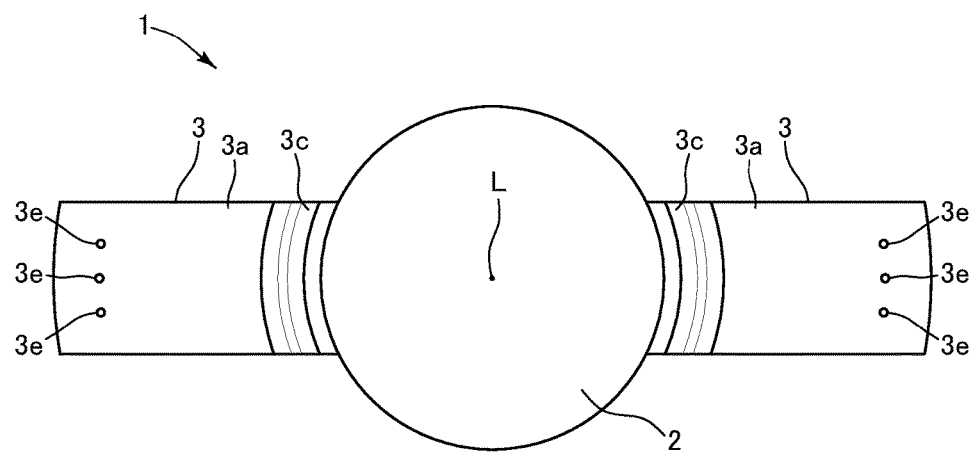
FIG. 8 is a schematic bottom view showing an intraocular lens obtained by removing the first projections from the intraocular lens in FIG. 1E.

In the above, the example in which the first projections 3*d* and the second projections 3*e* are provided to the intraocular lens 1 has been described. However, an intraocular lens having either the first projections 3*d* or the second projections 3*e* (see FIG. 7 and FIG. 8) may be formed. In addition, the number of first projections 3*d* and the number of second projections 3*e* may be variously changed. Furthermore, a plurality of projections such as a third projection and a fourth projection from each of which the distance to the axial line L as seen from the direction along the axial line L as shown in FIG. 1E is different from the distances L1 and L2 may be provided. Alternatively, an intraocular lens to which only a plurality of projections having different distances to the axial line L are provided may be formed.

DESCRIPTION OF THE REFERENCE CHARACTERS 1 intraocular lens
2 lens
3 haptic
3*a* main body (leg portion)
3*b* projecting portion
3*c* recess
3*d* first projection (projection portion)
3*e* second projection (projection portion)
4 eye
5 cornea
6 eye chamber
7 iris
8 ciliary body
9 ciliary process
10 ciliary zonule
11 crystalline lens
12 ciliary sulcus
C visual axis
L1 distance (first distance)
L2 distance (second distance)

The invention claimed is:

1. At least two planar haptics for holding a posterior chamber phakic intraocular lens (IOL) having an IOL axis, the IOL being configured to be disposed behind an iris in an eye of a patient so that the IOL axis is aligned with a visual axis of the patient, each of said at least two planar haptics, comprising:
   an elastically deformable plate-shaped leg portion having a posterior surface and an anterior surface and outwardly extending from the IOL in a radial direction about the IOL axis;
   a projecting portion projecting from a distal end of the leg portion substantially parallel to the IOL axis, the projecting portion being configured to be fitted into the ciliary sulcus in the eye of the patient;
   V-shaped grooves located on the anterior surface and the posterior surface of the leg portion, each of the V-shaped grooves forming an arch shape around the IOL axis; and
   a plurality of projections located around the IOL axis and projecting from the posterior surface of the leg portion substantially parallel to the IOL axis, each of the plurality of the projections being configured to project into a space between a plurality of ciliary zonules connecting a crystalline lens and a ciliary body in the eye, wherein
   the plurality of the projections further comprises ciliary-zonule-contacting surfaces, wherein each of the plurality of the projections is configured to be interposed and held between the plurality of ciliary zonules via the ciliary-zonule-contacting surfaces, whereby force which is transmitted from the ciliary body through the plurality of ciliary zonules to the crystalline lens is transmitted through the projection portion to the leg portion.

2. The haptics according to claim 1, wherein the plurality of the projections is grouped into a first row of the projections and a second row of the projections, a first distance between the IOL axis and each of the first row of the projections is different from a second distance between the IOL axis and each of the second row of the projections.

3. The haptics according to claim 1, wherein a distance between the IOL axis and each of the plurality of the projections is equal to each other.

4. The haptics according to claim 1, wherein the IOL is a lens for correcting astigmatism of the patient.

5. At least two planar haptics for holding a posterior chamber phakic intraocular lens (IOL) having an IOL axis, the IOL being configured to be disposed behind an iris in an eye of a patient so that the IOL axis is aligned with a visual axis of the patient, each of said at least two planar haptics, comprising:
- an elastically deformable plate-shaped leg portion having a posterior surface and outwardly extending from the IOL in a radial direction about the IOL axis;
- a projecting portion for projecting from a distal end of the leg portion substantially parallel to the IOL axis, the projecting portion being configured to be fitted into the ciliary sulcus in the eye of the patient; and
- a plurality of projections having at least two rows located around the IOL axis and projecting from the posterior surface of the leg portion substantially parallel to the IOL axis, the plurality of the projections alternate with each other between the two rows, each of the projections being configured to project into a space between a plurality of ciliary zonules connecting a crystalline lens and a ciliary body in the eye, wherein
the plurality of the projections further comprises ciliary-zonule-contacting surfaces, wherein each of the plurality of the projections is configured to be interposed and held between the plurality of ciliary zonules via the ciliary-zonule-contacting surfaces, whereby force which is transmitted from the ciliary body through the plurality of ciliary zonules to the crystalline lens is transmitted through the projection portion to the leg portion.

\* \* \* \* \*